(12) United States Patent
Port

(10) Patent No.: US 6,440,956 B1
(45) Date of Patent: Aug. 27, 2002

(54) BICYCLIC POLYAMINOACID METAL COMPLEXES, THEIR PROCESS OF PREPARATION AND THEIR APPLICATION IN MEDICAL IMAGING

(75) Inventor: Marc Port, Deuil la Barre (FR)

(73) Assignee: Guerbet, Villepinte (FR)

( * ) Notice: Subject to any disclaimer, the term of this patent is extended or adjusted under 35 U.S.C. 154(b) by 0 days.

(21) Appl. No.: 09/589,345

(22) Filed: Jun. 8, 2000

(30) Foreign Application Priority Data

Jun. 9, 1999 (FR) .............................. 99 07283

(51) Int. Cl.⁷ ..................... C07D 487/08; A61K 31/555
(52) U.S. Cl. ..................... 514/186; 540/465; 514/300; 534/10; 534/14; 534/16
(58) Field of Search .......................... 540/465; 514/186, 514/300; 534/14, 10, 16

(56) References Cited

U.S. PATENT DOCUMENTS 5,554,748 A * 9/1996 Sieving et al. .............. 540/465
5,886,158 A * 3/1999 Meyer et al. ................ 534/16

FOREIGN PATENT DOCUMENTS

WO    WO93/11800    6/1993

* cited by examiner

Primary Examiner—Richard L. Raymond
Assistant Examiner—Kahsay Habte

(74) Attorney, Agent, or Firm—Jacobson Holman, PLLC

(57) ABSTRACT

Metal chelates of the amides of formula

I

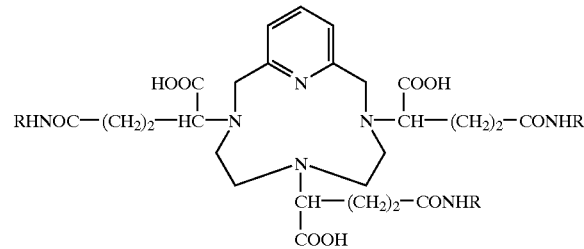

in which
R has the formula

II

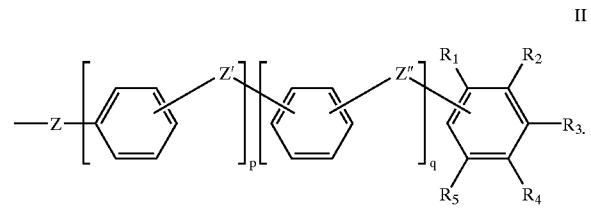

Use in medical imaging.

35 Claims, No Drawings

BICYCLIC POLYAMINOACID METAL COMPLEXES, THEIR PROCESS OF PREPARATION AND THEIR APPLICATION IN MEDICAL IMAGING

The present invention relates to metal chelates derived from a tetranitrogenous macrocycle condensed with a pyridyl nucleus, to their processes of preparation and to their application in medical imaging.

The use in imaging of chelates, with a paramagnetic or radioactive cation, of certain derivatives of this condensed macrocycle has been proposed on various occasions. Reference may be made to Patents EP-A-0,438,206, EP-A-0,570,575 and EP-A-0,579,802, which disclose compounds of formula

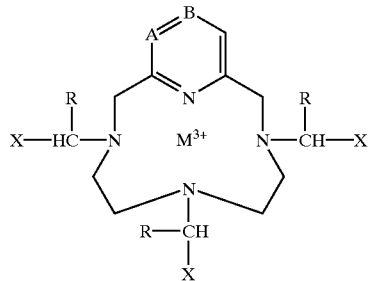

in which X can be a carboxylate or phosphate group and R can be an alkyl or phenyl group or one of the R groups is a group forming a bond with a biological macromolecule.

Among these compounds, that for which A=B=CH, R=H, X=$CO_2^-$ and M=Gd, known as PCTA, has been the subject of in-depth studies, described in Inorganic Chemistry, 36(14), 2992–3000 (1997) and Magn. Reson. Chem., 36, S200–208 (1998); the authors indicate in particular that PCTA is noteworthy in that it has a particularly high longitudinal relaxation $r_1$, since it is approximately "2 times" that of the gadolinium chelates used as contrast agents in magnetic resonance imaging in man.

It is known that $r_1$ characterizes the effectiveness of paramagnetic products in generating a strong contrast of the images and it is especially advantageous and unexpected that the paramagnetic products of the invention exhibit relaxations $r_1$ of 10 to 15 times greater than that of the commercial compounds, not only for a magnetic field of 0.5 tesla but also of 1 tesla, the field of most current imaging devices, and even at 1.5 tesla, the field of the devices with the best performances.

As these novel chelates, in addition to their favourable magnetic properties, are stable in vitro and in vivo, in particular with respect to possible breakdown of the complex, have a low osmolality and a good therapeutic index, and, according to the nature of the R group, can exhibit an excellent vascular persistence or an organ specificity, they will advantageously be used in man as contrast agents for magnetic resonance imaging or in nuclear medicine, when the metal ion is a radioelement.

The present invention relates to metal chelates of the compound of formula

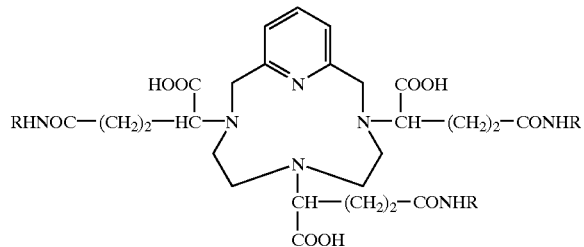

in which
R has the formula

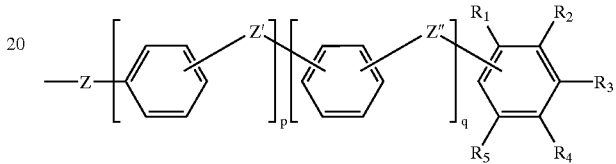

and

Z is a bond or a group selected from the $CH_2$, $CH_2$—CO—NH or $(CH_2)_2$—NH—CO groups, Z' is a bond or a group selected from the O, S, NQ, $CH_2$, CO, CO—NQ, NQ—CO, NQ—CO—NQ or CO—NQ—$CH_2$—CO—NQ groups, Z" is a bond or a group selected from the CO—NQ, NQ—CO or CO—NQ—$CH_2$—CO—NQ groups, p and q are integers, the sum of which has a value from 0 to 3, $R_1$, $R_2$, $R_3$, $R_4$ and $R_5$, independently of one another, are selected from the H, Br, Cl, I, CO—$NQ_1Q_2$ and $NQ_1$—CO—$Q_2$ groups, $Q_1$ and $Q_2$, which are identical or different, being H or ($C_1$–$C_6$)alkyl optionally interrupted by one or more oxygen atoms and at least one of the $R_1$ to $R_5$ groups being an amido group, or $R_1$, $R_3$ and $R_5$ are, independently of one another, H, Br, Cl or I, and $R_2$ and $R_4$ have the formula

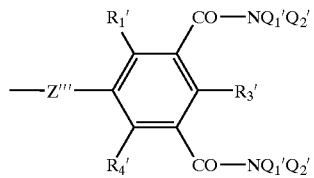

such that

Z''' is a group selected from the CO—NQ, CONQ—$CH_2$, CO—NQ—$CH_2$—CO—NQ, CO—NQ—$(CH_2)_2$—NQ—CO and NQ—CO—NQ groups and $R'_1$, $R'_3$ and $R'_5$, which are identical or different, are H, Br, Cl or I and $Q'_1$ and $Q'_2$, which are identical or different, are H or ($C_1$–$C_6$)alkyl optionally interrupted by one or more oxygen atoms, Q is H or ($C_1$–$C_4$)alkyl, the alkyl groups being optionally mono- or polyhydroxylated.

The metal ions can be paramagnetic ions, such as $Gd^{3+}$, $Fe^{3+}$, $Tb^{3+}$, $Mn^{2+}$, $Dy^{3+}$ or $Cr^{3+}$, or radioactive ions, such as $^{99m}$Tc, $^{67}$Ga or $^{111}$In; the ions which form less stable chelates, which can give rise to transmetallation, such as $Ca^{2+}$ or $Zn^{2+}$, also form part of the invention; the paramagnetic chelates of $Gd^{3+}$ and $Mn^{2+}$ are particularly suited to magnetic resonance imaging. The paramagnetic chelates of $Gd^{3+}$ are very particularly preferred.

It is preferable, for better hydrophilicity and biocompatibility of the compounds, for the $R_1$ to $R_5$ groups on the same phenyl ring together to comprise from 6 to 20 OH groups or even for any $CONQ_1Q_2$ group present, or, depending on the situation, $CONQ'_1Q'_2$, to comprise from 6 to 10 OH groups; it is also preferable for $R_2$ and $R_4$ to be identical and to be $CO-NQ_1Q_2$, which each comprise 6 to 10 OH groups, or the III group, in which each $CONQ'_1Q'_2$ comprises from 6 to 10 OH groups; preference is also given to the compounds in which $R_1$, $R_3$ and $R_5$ are selected from iodine or bromine atoms, as well as $R'_1$, $R'_3$ and $R'_5$, when they are present.

The relaxation of the compounds and their in vivo pharmacokinetics depend in particular on their number of phenyl ring. For example, it is possible to distinguish the compounds in which p and q are 0, in particular when $R_2$ and $R_4$ are $CO-NQ_1Q_2$, and those in which the sum of p and q has a value from 1 to 3 or better still 1 or 2 and $R_2$ and $R_4$ are or have not the formula III.

When, in the compounds of formula I, $R_2$ and $R_4$ are $CONQ_1Q_2$, $Q_1$ and $Q_2$ are preferably $C_2$ to $C_6$ alkyl groups optionally interrupted by an oxygen atom.

Furthermore, preference is given, among the compounds of formula I, to those in which Q is H and, among these, to those in which Z is $CH_2$ or $CH_2CONH$, Z' is a group selected from CONH, CONHCH$_2$CONH or NHCONH and Z" from CONH and CONHCH$_2$CONH, and it is also preferable, when it is present, for Z''' to be CONH or CONHCH$_2$CONH.

Finally, another group of specific compounds is composed of that in which, p and q being equal to 1, Z is $CH_2$ or $CH_2CONH$, Z' and Z" are selected from CONH and CONHCH$_2$CONH, and $R_2$ and $R_4$ are $CONQ_1Q_2$, with $R_1$, $R_3$ and $R_5$ preferably selected from Br and I.

Other preferred compounds are those defined in points (i) to (ix) hereinbelow:

(i) chelate of the compound of formula I in which p and q are 0 and $R_2$ and $R_4$, which are identical, are $-CO-NQ_1Q_2$, each $-CO-NQ_1Q_2$ group comprising from 6 to 10 —OH groups;

(ii) chelate of the compound of formula I in which p and q are 0, $R_1$, $R_3$ and $R_5$ are identical and are selected from Br and I, and $R_2$ and $R_4$, which are identical, are $-CO-NQ_1Q_2$, each $-CO-NQ_1Q_2$ group comprising from 6 to 10 —OH groups;

(iii) chelate of the compound of formula I in which the sum p+q is not 0, any $-CO-NQ_1Q_2$ group present comprises from 6 to 10 —OH groups, and $R_2$ and $R_4$ have not the formula III. Among these compounds, those for which p+q is 1 or 2 are more preferred.

(iv) Chelate of the compound of formula I in which the sum p+q is not 0, $R_1$, $R_3$ and $R_5$ are identical and are selected from Br and I, and $R_2$ and $R_4$, which are identical, are $-CO-NQ_1Q_2$, $R_2$ and $R_4$ each comprising from 6 to 10 —OH groups. Among these compounds, those for which p+q is 1 or 2 are more preferred.

(v) Chelate of the compound of formula I in which Z is $CH_2$ or $CH_2-CO-NH$, Z' is a group selected from CO—NH, CO—NH—CH$_2$—CO—NH and NH—CO—NH, Z" is a group selected from CO—NH and CO—NH—CH$_2$—CO—NH, $R_2$ and $R_4$, which are identical, are —CO—NQ$_1$Q$_2$, $R_2$ and $R_4$ each comprising from 6 to 10 —OH groups, and $R_1$, $R_3$ and $R_5$ are identical and are selected from Br and I. Among these compounds, those for which p+q is 1 or 2 are more preferred.

(vi) Chelate of the compound of formula I in which Z is $CH_2$ or $CH_2-CO-NH$, Z' is a group selected from CO—NH, CO—NH—CH$_2$—CO—NH or NH—CO—NH, Z" is selected from CO—NH and CO—NH—CH$_2$—CO—NH, Z''', when it is present, is CO—NH or CO—NH—CH$_2$—CO—NH, and the sum p+q is 1 or 2;

(vii) chelate of the compound of formula I in which $R_2$ and $R_4$ are $CONQ_1Q_2$ and $Q_1$ and Q2 are polyhydroxylated $C_2$ to $C_6$ alkyl groups optionally interrupted by an oxygen atom;

(viii) chelate of the compound of formula I in which Z is $CH_2$ or $CH_2-CO-NH$, Z' and Z" are selected from CO—NH and CO—NH—CH$_2$—CO—NH, p and q are equal to 1, and $R_2$ and $R_4$ are $CONQ_1Q_2$. Preference is given, among these compounds, to those for which:
→ $R_2$ and $R_4$ together comprise from 6 to 20 OH groups, or
→ $R_1$, $R_3$ and $R_5$ are identical and are selected from Br and I, and $R_2$ and $R_4$ each comprise from 6 to 10 OH groups.

(ix) Chelate of the compound of formula I in which the sum p+q is 0, $R_2$ and $R_4$ are the formula III and $R_1$, $R_3$ and $R_5$ are identical and are selected from Br and I.

The invention also relates to a process for the preparation of the compounds of formula I which consists in reacting the condensed macrocycle of formula

IV

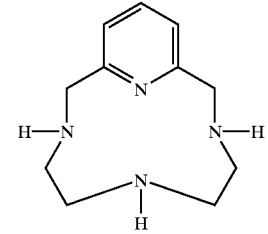

with a compound of formula R'OOC—CHX—(CH$_2$)$_2$—COOR', in which X is a leaving group, such as a halogen atom, preferably bromine, or a (C$_1$–C$_3$) alkanesulphonate, tosylate or triflate group, and R' is H or (C$_1$–C$_3$) alkyl or benzyl, and in hydrolysing or hydrogenating the ester functional groups when R' is other than H, in order to obtain the hexaacid of formula

V

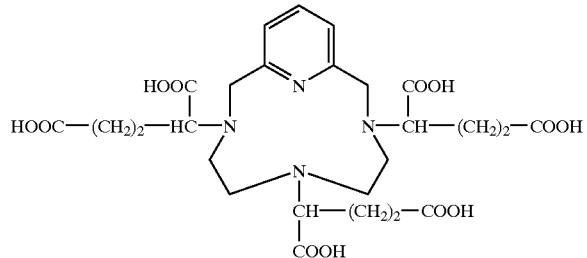

in then reacting a salt or an oxide of the metal to be complexed with the hexaacid, in order to obtain the corresponding chelate or one of its salts with a base, and, finally, in reacting the amine $RNH_2$, in which R has the same meaning as in the formula I, with the chelate in the presence of an agent for activating the carboxylic acid functional groups, in order to obtain the triamide of formula I.

The acid of formula V and its metal chelates, in particular that of gadolinium, and their salts with a base, such as NaOH, which are intermediates in the synthesis of the products of formula I, are another subject-matter of the invention.

The invention also relates to compositions comprising a compound of formula I for magnetic resonance imaging, when M represents a paramagnetic cation, or for nuclear medicine, when M represents a radioelement, or for radiology, when M is the cation of a heavy atom which absorbs X-rays, it being possible for the said compositions to comprise the additives and vehicles usual for oral or parenteral administration.

Finally, the invention relates to medical imaging methods which consist in administering a composition comprising a compound of formula I to the patient and in observing the region to be studied obtained by magnetic resonance, by scintigraphy or using X-rays.

The diagnostic compositions of the invention can comprise, with a compound of formula I, additives such as antioxidants, buffers, osmolality regulators, stabilizers, calcium, magnesium or zinc salts, or low proportions of other chelates of these cations or of complexing compounds. Formulation examples appear in the general literature and in particular in Remington's for Pharmaceutical Science, 18th Edition (1990), Mack. Pub. Co.

The unit doses will depend on the nature of the contrast agent, on the administration route, on the patient and in particular on the nature of the disorder to be studied. For intravenous injection and observation by magnetic resonance, the concentration of the solution will be between 0.001 and 0.5 mol/liter and, depending on the circumstances, from 0.001 to 0.1 millimol/kilo will be administered to the patient.

The contrast agents of the invention can be used to visualize the brain, organs such as the heart, liver or kidneys and all or part of the vascular system and to study the perfusion of these regions and to characterize permeability, tumoral, inflammatory or ischaemic anomalies.

The various stages of the synthesis of the compounds of the invention are carried out under conditions analogous to those described in the literature for reactions of the same type.

The macrocycle of formula IV can be prepared by the method of Richman and Atkins described in Inorg. Chem., 32, 5257–5265 (1993).

The nitrogen atoms are substituted, for example, by the action of an α-bromoglutaric ester in the presence of an inorganic or organic base, such as NaOH, $Na_2CO_3$ or $N(C_2H_5)_3$, in solution in a polar solvent, such as an alcohol, or, preferably, an aprotic solvent, such as acetonitrile or tetrahydrofuran.

The ester functional groups are hydrolysed by the action of a base or of an acid in aqueous or aqueous/alcoholic medium.

The complexing is carried out conventionally, for example as disclosed in U.S. Pat. No. 5,554,748 or in Helv. Chim. Acta, 69, 2067–2074 (1986).

To obtain the gadolinium chelate, $GdCl_3$ or $Gd_2O_3$ can be reacted with the compound of formula V in aqueous solution at a pH of between 5 and 6.5. The cation of a complex derived from a compound of formula V or I can also be exchanged, when the relative stability of the two complexes permits it, in particular with an ion-exchange resin.

The relative percentage of the isomers in the mixture obtained, due to the presence of the three asymmetric carbons, can be modified by maintaining an aqueous solution of the chelate with a pH in the region of 3 at a temperature of greater than 80° C. for a few days.

The amidation reaction can be carried out in aqueous medium, optionally in the presence of a third solvent, such as dioxane or tetrahydrofuran, with an activating agent, such as a soluble carbodiimide, for example those carrying an amine group described in J. Org. Chem., 21, 439–441 (1956) and 26, 2525–2528 (1961) or disclosed in U.S. Pat. No. 3,135,748 or carrying a quaternary ammonium group described in Org. Synth. V, 555–558, which relates to 1-ethyl-3-(3-dimethylaminopropyl)carbodiimide (EDCI) and 1-cyclohexyl-3-(2-morpholinoethyl) carbodiimide metho-p-toluenesulphonate. It can also be carried out with N-hydroxysulphosuccinimide, as described in Bioconjugate Chem., 5, 565–576 (1994), or 2-succinimido-1,1,3,3-tetramethyluronium tetrafluoro-borate and analogues, described in Tetrahedron Letters, 30, 1927–1930 (1989).

Another process consists in forming an intermediate activated ester by reacting, for example, N-hydroxysulphosuccinimide (NHS) or hydroxybenzotriazole (HOBT) in the presence of carbodiimide, such as EDCI, with the chelate V, which can be dissolved by salification with an inorganic cation, for example an ammonium or sodium.

With 2-ethoxy-l-ethoxycarbonyl-1,2-dihydro-quinoline (EEDQ), the reaction can be carried out in aqueous/alcoholic medium.

Some of the $RNH_2$ amines are known compounds; the others will be prepared by analogous processes, preferably by attaching the phenyl nuclei step by step from the phenyl comprising the $R_1$ to $R_5$ groups and a substituent which is suitable for forming, depending on the circumstances, Z, Z' or Z".

Reference may also be made to Patents WO 96/09281 or WO 97/01359 for the preparation of those in which Z is $CH_2CONH$, p=q=0, $R_1=R_3=R_5$=halogen or H, and $R_2=R_4=CONQ_1Q_2$.

In some of the precursor aminoalcohols $HNQ_1Q_2$, $Q_1$ and/or $Q_2$ represent the $CH_2(CHOH)_n(CH_2OCH_2)_r(CHOH)_t$ $CH_2OH$ group with t=0, r=0 or 1 and n=0 to 4; they can be prepared from a primary alkylamine or aminoalcohol, with which a sugar is reacted, before carrying out the reduction of the imine obtained, as disclosed in EP-A-675105 or EP-A-558395, or from benzylamine, with which a sugar and then an optionally hydroxylated $C_1$–$C_6$ alkyl sulphate or halide are reacted, before removing the benzyl group by catalytic hydrogenation.

Different stereoisomers will be obtained, depending on the configuration of the sugar reacted.

The aminoalcohols can, when r=1 and n=t=0, be prepared from 2-aminoethoxyethanol, with which is reacted a suitably hydroxylated alkyl halide or epoxide or alternatively a hydroxylated aliphatic aldehyde, such as a monosaccharide, in order to form an imine, subsequently reduced catalytically or chemically.

When r=n=1, the aminoalcohols can be prepared by reaction of the epoxide

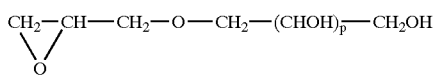

with the appropriate primary aminoalcohol, the said epoxides being obtained by oxidation of the corresponding ethylenated derivatives by a peracid or a peroxyimidic acid, as described in J. Org. Chem., 26, 659–663 (1961) and 48, 888–890 (1983).

Mention may be made, among the aminoalcohols prepared by these methods, of those for which $Q_1=CH_2(CHOH)_4$ $CH_2OH$ and $Q_2=Q_1$ or $CH_2$ (CHOH) $CH_2OH$ $Q_1=CH_2(CHOH)_2CH_2OH$ and $Q_2=CH_2CHOHCH_2O(CH_2)_2OH$ or $(CH_2)_2OCH_2CHOHCH_2OH$ $Q_1=CH_2(CHOH)_3CH_2OH$ and $Q_2=(CH_2)_2O(CH_2)_2OH$.

In the case where p and/or q are other than zero, the Z" bridge will be formed between the two phenyl nuclei, depending on the circumstances, before or after the Z' bridge.

For example, the compound

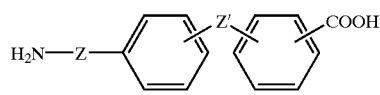

VI can be prepared, when Z is a bond, from the diphenyl derivatives VII or their esters.

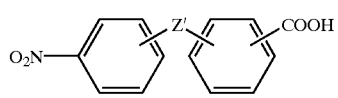

VII in which Z' has the same meaning as in the formula II.

The compound VII in which Z' is O is described in Makromoleculare Chemie, 130, 103–144 (1969), that in which Z' is NH is described in Indian J. Chem., 13, 35–37 (1975), that in which Z' is $CH_2$ or CO is described in J. Pharm. Sci., 55(3), 295–302 (1966), that in which Z' is a bond is described in Synth. Comm., 24(22), 3307–3313 (1994) and that in which Z' is S is described in Il Farmaco, 44(7–8), 683–684 (1989).

Other compounds vII can be prepared by analogous processes; for example, when Z' is HNCONH, by reaction of $O_2NC_6H_4NCO$ with $H_2NC_6H_4COOH$ in anhydrous medium or, when Z' is NHCO or CONH, by reaction of the aromatic acid chloride with the appropriate aniline in solution in an aprotic solvent, such as $CH_2Cl_2$, $C_6H_5CH_3$ or $CH_3CON(CH_3)_2$, or by reaction of the aromatic acid with the aniline in the presence of sulphonic acid chloride, of triethylamine and of dimethylaminopyridine, as described in Synth. Communications, 25(18), 2877–2881 (1995).

The reduction of the $NO_2$ group of VII to $NH_2$ can be carried out in a known way with hydrogen in the presence of catalysts or chemically.

When Z in the formula VI is $CH_2$—CONH, glycine, the acidic functional group of which is activated and the $NH_2$ group of which is protected, is reacted with a compound VI in which Z is a bond or with aniline carrying a precursor group for Z', which is optionally protected.

The glycine is protected, for example, in the carbamate form, in particular t-butyl carbamate (Synthesis, 48,(1986)) and benzyl carbamate (Chem. Ber., 65, 1192 (1932)), in the phthalimide form (Tetrahedron Letters, 25, 20, 2093–2096 (1984)), with a benzyl (Bull. Soc. Chim. Fr., 1012–1015 (1954)) or with an N-allyl (Tetrahedron Letters, 22, 16, 1483–1486 (1981)). (See also Protective Groups in Organic Synthesis, 315–349, T. W. Greene (John Wiley & Sons Inc.)). The protective group for the $NH_2$ attached to Z is generally removed only after the R group has been constructed; conventionally, a phthalimido group is removed by the action of hydrazine, whereas a benzyloxycarbonyl or benzyl group is removed by catalytic hydrogenation.

When $Z=CH_2$ and $Z'=CONH$ or $CONHCH_2CONH$, 4-aminomethylbenzoic acid, in which the $NH_2$ group is protected in the carbamate or imide form as described in J. Org. Chem., 43, 2320–2325 (1978) or in Rec. Trav. Chim. Pays-Bas, 79, 688 (1960), can be reacted with the substituted benzoic acid, the acidic functional group of which is blocked by esterification.

When Z is $(CH_2)_2NHCO$, $RNH_2$ can be prepared by reaction of an excess of ethylenediamine with an appropriate benzoic ester carrying a precursor group for Z', which is optionally protected, or a more complete fraction of R.

The compound VI, after protection of the $NH_2$ group and activated in the acid chloride form or by a peptide coupling agent, will react with the precursor group for Z" carried by the terminal phenyl nucleus, suitably substituted by $R_1$ to $R_5$, to give $RNH_2$ after deprotection.

The conditions for the preparation of the $RNH_2$ amines will be better understood on reading the examples which follow. The mass spectra (electrospray) of these products, such as those of the examples, correspond to the expected structures.

Compounds A and A'

$RNH_2$ with

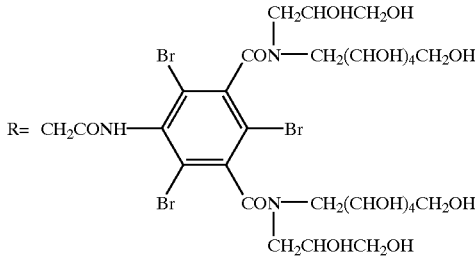

Compound A (a) 1-Deoxy-1-(2,3-dihydroxypropyl)amino-D-galactitol from α-D-galactose 35 g of D-galactose are dissolved in 100 ml of methanol comprising 17 g of 3-aminopropanediol and the mixture is kept stirred at 25° C. for 12 hours, before introducing 5 g of 10% palladium-on-charcoal catalyst and 40 ml of water in order to hydrogenate the imine at 60° C. The catalyst is removed by filtration and the mixture is concentrated to 85 ml. The aminoalcohol is isolated by precipitation when the concentrated solution is introduced into 30 ml of isopropanol at approximately 35° C.

(b) 5-Amino-2,4,6-tribromoisophthalic acid 156 g of bromine are slowly introduced into 300 ml of an aqueous solution of 50 g of 5-aminoisophthalic acid and 55 ml of 37% hydrochloric acid. After stirring overnight, the excess bromine is neutralized by addition of an aqueous sodium bisulphite solution, before isolating the precipitate. Yield: 90%.

(c) 5-(Phthalimidoacetamido)-2,4,6-tribromoisophthalic acid 27 ml of thionyl chloride are slowly introduced into a solution of 69 g of N-phthaloylglycine in 200 ml of dimethylacetamide at 10° C. and then, after stirring for 2 hours, 100 g of the acid obtained above are introduced at approximately 15–20° C. After leaving overnight at room temperature, the mixture is poured into 800 ml of warm water. 140 g of final product are thus isolated.

(d) Chloride of the Preceding Diacid 70 ml of thionyl chloride are slowly introduced at 18° C. into a solution of 100 g of the diacid in 300 ml of dioxane and 50 ml of dimethylformamide. The yellow precipitate formed after stirring for 3 days at room temperature is filtered off and washed with methyl t-butyl ether. 70 g of beige solid are thus obtained.

(e) N,N'-Bis(2,3,4,5,6-pentahydroxyhexyl)-N,N'-bis(2,3-dihydroxypropyl)-2,4,6-tribromo-5-(phthalimidoacetamido)isophthalamide 125 g of the galactitol-derived amine obtained in (a) are dissolved in 610 ml of N-methylpyrrolidone at 80° C. before introducing, at 60° C., 17 g of $Na_2CO_3$ and 102 g of the diacid chloride. After two hours at this temperature, the reaction mixture is brought back to room temperature and then filtered. The filtrate is introduced into 1.5 liters of isopropanol; the precipitate formed is dissolved in water and chromatographed on an ion-exchange resin in the $H^+$ form in order to remove the starting amine. 136 g of solid product are thus isolated.

(f) Compound A 125 g of the preceding phthalimide are dissolved in 520 ml of N-methylpyrrolidone and 175 ml of water at 70° C and 8 ml of hydrazine hydrate are added before maintaining the mixture for two hours at 90° C. This mixture is subsequently cooled to approximately 20° C. and then poured into 1.6 liters of ethanol. The precipitate formed is purified by passing its aqueous solution through an ion-exchange resin in the $H^+$ form.

Compound A'

(a') By reacting 3-aminopropanediol with D-glucose under the same conditions as described hereinabove in stage (a) for the preparation of the compound A, 1-deoxy-1-(2,3-dihydroxypropyl)amino-D-glucitol is obtained.

The compound A' can be obtained by carrying out stages (b) to (f) described hereinabove for the preparation of the compound A from the glucitol-derived amine obtained in (a') or else by carrying out the following stage (e').

(e') 95 g of the glucitol-derived amine obtained in (a') are dissolved in 460 ml of dimethylacetamide at 90° C. before introducing, at 65° C., 32 ml of triethylamine and 117 g of the diacid chloride described in the above stage (d) in the preparation of the compound A. After 4 h 30 at 55–60° C., the reaction mixture is brought back to room temperature and filtered. The solution obtained, at 50° C., is slowly poured into an aqueous hydrazine solution (11 ml in 115 ml of water) ; after 3 hours at 80° C., the mixture, brought back to room temperature, is acidified to pH 1 by addition of an N aqueous HCl solution. The precipitate is separated off and the filtrate is poured into 3 liters of ethanol with stirring. The precipitate formed is dried and then purified by diafiltration, in order to remove most of the molecules of low mass, and the solution obtained is chromatographed on anion- and cation-exchange resins. Yield 60%.

The final amine can be freeze-dried.

HPLC analysis on Column 2 with Eluent 2: $CF_3COOH$ in water pH 3.3/$CH_3CN$

Compound B $RNH_2$ with

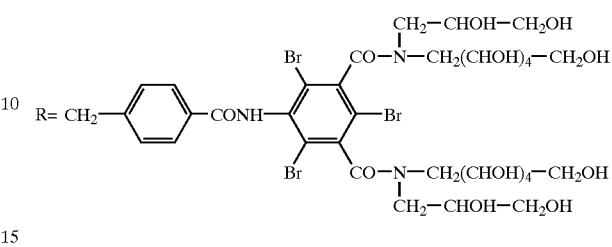

(a) 4-Phthalimidomethylbenzoic acid

A mixture of 10 g of 4-aminomethylbenzoic acid, 14.5 g of carbethoxyphthalimide, 9.2 ml of triethylamine and 140 ml of tetrahydrofuran is maintained for 72 hours at reflux temperature. The precipitate formed is isolated at room temperature; after washing with an aqueous acidic solution and drying, 14.5 g of product are obtained. M.p.=264° C.

(b) Chloride of the Preceding Acid 1 g of tricaprylylmethylammonium chloride (Aliquat® 336) and 5.3 ml of thionyl chloride are introduced into a solution of 13.5 g of the acid in 55 ml of dioxane. After stirring for 12 hours at 80° C., the mixture is concentrated to dryness and the residual solid is washed with diisopropyl ether. w=14 g.

(c) 2,4,6-Tribromo-5-(phthalimidomethylbenzamido)isophthalic acid 14 g of the acid chloride and 15 g of 5-amino-2,4,6-tribromoisophthalic acid are dissolved in 50 ml of N-methylpyrrolidone and the mixture is maintained at 100° C. for several hours. The solution, at approximately 20° C., is poured into 300 ml of water and the precipitate formed is recrystallized from isopropanol to give 5.5 g of final product.

HPLC (high performance liquid chromatography): Column No. 1: Symmetry® C18; 100 Å; 5 μm; l=25 cm; d=4.6 mm (Waters).

Eluent No. 1: $CH_3COONH_4$ in water (0.005 M)/$CH_3CN$.

Gradient: 80% to 20% (v/v) over 15 minutes; Flow rate 1 ml/minute;

$t_r$=4.5 minutes.

(d) Chloride of the Preceding Acid 5.6 ml of dimethylformamide and 9 ml of thionyl chloride are introduced into a solution of 5.5 g of the acid in 40 ml of dioxane while maintaining the temperature at less than 5° C. After 30 minutes, the mixture is poured into 150 ml of water and the precipitate formed is isolated. w=4.6 g.

(e) Compound B 2.3 g of the acid chloride are introduced into a solution of 4 g of the aminoalcohol 1-deoxy-1-(2,3-dihydroxypropyl)amino-D-galactitol in 15 ml of N-methylpyrrolidone at 65° C. After 3 hours 30, 4 ml of water are added and the mixture is brought to 90° C. before adding 0.3 ml of hydrazine hydrate. After 2 hours at 90° C., the solution is poured, at room temperature, into 80 ml of ethanol. The isolated precipitate is dissolved in 10 ml of water and the solution, at pH 1, is purified by chromatography through an anionic resin in the OH⁻ form, of the Amberlite® type, then through a cationic resin in the H⁺ form, of IMAC® type, and finally through an OH⁻ anionic resin. 2 g of amine are obtained.

HPLC: Column No. 2: LiChrospher®; 100 RP18; 5 μm; 1=25 cm; d=4 mm (Merck®).

Eluent No. 2: $CF_3COOH$ in water pH 3.3/$CH_3CN$.

Gradient: 98% to 77% (v/v) over 25 minutes; Flow rate 1 ml/minute;

$t_r$: 18 to 22 minutes.

Compound C $RNH_2$ with

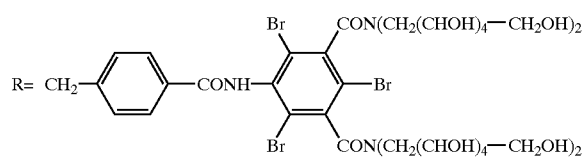

2.3 g of the acid chloride prepared according to the preceding stage (d) are introduced into a solution at 65° C. of 5.5 g of disorbitylamine in 30 ml of N-methylpyrrolidone. After 4 hours at 65° C., 8 ml of water are introduced and then, at 90° C., 0.3 ml of hydrazine hydrate; after 2 hours at this temperature, the reaction mixture, at approximately 20° C., is poured onto 130 ml of water. The precipitate formed is washed with ethanol and then redissolved in 10 ml of water, and the solution is brought to a pH of 1.5 and then purified by chromatography through anionic and cationic resins. 1.7 g of the amine are thus obtained.

HPLC: Column No. 2; Eluent No. 2;

$t_r$: 18 minutes.

Compound D $RNH_2$ with

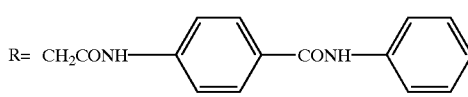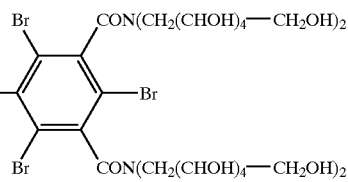

(a) N,N'-[bis(2,3,4,5,6-pentahydroxyhexyl)]-2,4,6-tribromo-5-(glycylamino)isophthalamide 1. 15 g of disorbitylamine are dissolved in 60 ml of N-methylpyrrolidone at 80° C. and 1.6 g of dry sodium carbonate are introduced into the mixture at 60° C., followed by 9.6 g of 5-(phthalimidoacetamido)-2,4,6-tribromoisophthalic acid chloride. After stirring for 1 hour at this temperature and 16 hours at room temperature, the precipitate is removed and the solution is poured into 160 ml of isopropanol. The isolated precipitate weighs 20 g.

2. Hydrazinolysis:

20 g of the preceding product and 1.7 ml of hydrazine hydrate are introduced into 40 ml of water at 70° C. After stirring for 3 hours, the mixture is acidified to pH 4 by addition of 6N hydrochloric acid at room temperature. The precipitate formed is then removed and the filtrate neutralized by addition of a 1N aqueous NaOH solution. The excess hydrazine is removed by reverse osmosis. The residual solution is treated with 1 ml of strong cationic resin and then 6.5 ml of weak anionic resin.

The final product is then extracted from the solution by attaching to a strong cationic resin in the H⁺ form, from where it is eluted with a dilute aqueous NaCl solution (0.1M). w=8 g.

HPLC: Column No. 2; Eluent No. 3;

Gradient: $CF_3COOH$ in water (pH 3.4)/$CH_3CN$ from 95% to 50% (v/v) over 50 minutes; flow rate 1 ml/minute;

$t_r$: 7 minutes.

(b) 4-[4-Nitrobenzamido]benzoic acid 10 g of 4-nitrobenzoic acid chloride are slowly introduced into 7.4 g of 4-aminobenzoic acid and 36 ml of dimethylacetamide while maintaining the temperature at less than 25° C. After stirring for 24 hours, 50 ml of methylene chloride are added at 10° C. in order to precipitate the desired product. After washing with water and drying, 14.5 g of product are isolated.

(c) 4-[4-Aminobenzamido]benzoic acid

A suspension of 13.6 g of the preceding acid in 180 ml of water, to which has been added 24 ml of 1N aqueous NaOH solution and 1.4 g of palladium-on-charcoal (10%), is subjected to a hydrogen pressure of 0.6 MPa for 4 hours.

The pH of the final suspension is then brought to approximately 10 before filtration through Celite® in order to remove the catalyst. The precipitate formed during the acidification of the filtrate to pH 5.3 is isolated and dried.

w=10.6 g; M.p. >260° C.

(d) 4-[4-(Phthalimidoacetamido)benzamido]benzoic acid 3.2 ml of thionyl chloride are introduced dropwise into a solution of 9 g of phthalimidoacetic acid in 40 ml of dimethylacetamide at 10° C. and then, after stirring for 3 hours, 10.5 g of the amino acid obtained previously are introduced at a temperature of less than 20° C.

After stirring for 12 hours, the mixture is poured into 400 ml of water and the isolated precipitate is washed with warm water. Weight after drying: 18 g. M.p. >260° C.

(e) Chloride of the Preceding Acid 2.5 ml of thionyl chloride are introduced into 10 g of the acid suspended in 50 ml of dioxane and 1 ml of dimethylformamide, and the mixture is kept stirred at 50° C. for 5 hours. After addition of one volume of diisopropyl ether, 10 g of precipitate are isolated.

The acid can also be suspended in toluene with tricaprylylmethylammonium chloride as catalyst.

(f) N,N'-bis(2,3,4,5,6-pentahydroxyhexyl)-2,4,6-tribromo-5-(4-[4-(phthalimidoacetamido)benzamido] benzoylglycylamino)isophthalamide A solution of 2.25 g of the acid chloride with 5 g of N,N'-bis(2,3,4,5,6-pentahydroxyhexyl)-2,4,6-tribromo-5-(glycylamino)isophthalamide and 0.7 ml of triethylamine in 25 ml of dimethylacetamide or of N-methylpyrrolidone is kept stirred for 12 hours and then poured into 60 ml of ethanol. 6.2 g of precipitate are thus isolated.

HPLC: Column No. 2; Eluent No. 3;

$t_r$=27–35 minutes (mixture of isomers).

(g) Hydrazinolysis

A solution of 0.6 ml of hydrazine hydrate in 10 ml of water is introduced into a solution of 10 g of the preceding phthalimide in 40 ml of dimethylacetamide at 80° C. After stirring for 3 hours at this temperature, the cooled mixture is poured into 125 ml of ethanol. 9 g of precipitate are isolated, which product is purified by treatment of its aqueous solution with a strong anionic (OH⁻) resin and then a weak cationic (H⁺) resin.

w=8 g.

The reaction mixture can also be acidified in order to separate the precipitated phthalohydrazide and to remove the solvent and the molecules of low mass by ultrafiltration, before final precipitation from aqueous ethanol.

HPLC: Column No. 2; Eluent No. 3 but 90/10 (v/v) in isochratic elution at 1 ml/minute;

$t_r$=28–35 minutes.
Compound E
RNH₂ with 140 ml of tetrahydrofuran is maintained at its reflux temperature for 72 hours. The precipitate, isolated by filtration at room temperature from the reaction mixture, is washed with diethyl ether and a 1N aqueous hydrochloric acid solution. 14.5 g of solid are obtained, 12.2 g of which are dissolved at 10° C. in 90 ml of N,N-dimethylacetamide and 3.5 ml of thionyl chloride; after stirring for 3 hours, 23.4 g of the aniline obtained in the preceding stage are introduced into the mixture and the mixture is left stirring overnight, before being poured into 900 ml of water. The isolated precipitate, washed with water, is recrystallized from 200 ml of dioxane.

w=30 g.

HPLC: Column No. 2; Eluent: CF₃COOH in H₂O (0.1M)/ CH₃CN (90/10, v/v) with a gradient after 20 minutes up to 40/60 over 30 minutes; flow rate 1 ml/minute;

$t_r$=26 to 29 minutes.

(d) Acid Dichloride 30.3 g of the isophthalic derivative obtained in the preceding stage are dissolved in 150 ml of dioxane comprising 26 ml of dimethylformamide and 42 ml of thionyl chloride are introduced dropwise at 5° C. After 30 minutes at 0° C., the mixture is poured into 550 ml of water and the precipitate formed is filtered off and washed with water and with diisopropyl ether. w=26 g after drying.

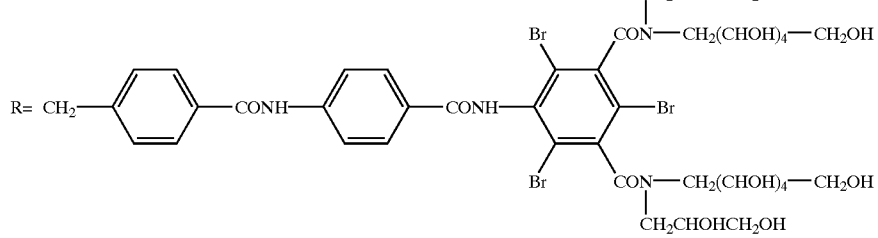

(a) 5-(4-Nitrobenzamido)-2,4,6-tribromoisophthalic acid 50 9 of para-nitrobenzoic acid chloride and 75 g of 5-amino-2,4,6-tribromoisophthalic acid in 400 ml of dioxane are maintained for 18 hours at the reflux temperature. After cooling, the precipitate is filtered off, washed with 50 ml of dioxane and dried.

w=115 g.

(b) 5-(4-Aminobenzamido)-2,4,6-tribromoisophthalic acid

A solution of 180 g of the preceding nitro derivative in 600 ml of water is brought to pH 6 by addition of a 5N aqueous NaOH solution and hydrogenated under a pressure of 5×10⁵ Pa in the presence of type 156 Pt (Johnson Matthey) for 7 hours. The catalyst is separated off by filtration and the water is evaporated under reduced pressure. w=80 g.

HPLC: Column No. 2; Eluent No. 4; CF₃COOH in water (pH 2.8) with methanol (99/1, v/v); flow rate 1 ml/minute;

$t_r$: 3.6 minutes (18.8 minutes for the nitro derivative).

(c) 5-(4-[4-(Phthalimidomethyl)benzamido) benzamido)-2,4,6-tribromoisophthalic acid A mixture of 10 g of 4-aminomethylbenzoic acid, 14.5 g of N-carbethoxyphthalimide and 9.2 ml of triethylamine in (e) N,N'-Bis(2,3,4,5,6-pentahydroxyhexyl)-N,N'-bis (2,3-dihydroxypropyl)-2,4,6-tribromo-5-[4-(4-amino-methylbenzamido)benzamido]isophthalamide 1. 10 g of the acid dichloride are introduced into a solution of 15 g of 1-deoxy-1-(2,3-dihydroxypropyl)amino-D-galactitol in 100 ml of N-methylpyrrolidone at 60° C. After stirring for 4 hours at this temperature, the mixture, brought back to room temperature, is poured into 1 liter of isopropanol. The precipitate formed is isolated and dried.

HPLC: Column No. 2; Eluent No. 5: CH₃COONH₄ in H₂O (0.01M) /CH₃CN; 85% to 50% (v/v) gradient over 20 minutes; flow rate 1 ml/minute;

$t_r$=16 minutes. 2. Removal of the phthalimide group:

20.4 g of the preceding solid are introduced with stirring into 80 ml of N,N-dimethylacetamide at 80° C., followed by 1.6 ml of hydrazine hydrate in solution in 20 ml of water. After 3 hours at this temperature, the reaction mixture is poured at room temperature into 1 liter of ethanol. The precipitate formed is isolated, dried and then dissolved in 40 ml of water. Approximately 2 ml of 6N aqueous HCl solution are introduced at 0° C. in order to lower the pH to 2; the mixture is filtered through Celite® and then purified by passing through ion-exchange resins (anionic Amberlite® and cationic IMAC®). 6 g of the desired product are then obtained.

HPLC: Column No. 2; Eluent No. 5

$t_r$=24 to 29 minutes.

Compound F $RNH_2$ with:

Analytical HPLC: Column No. 2; Eluent No. 8

Product obtained in the corresponding stage (a): $t_r$=7 to 24 minutes

Final product: $t_r$=30 to 40 minutes.

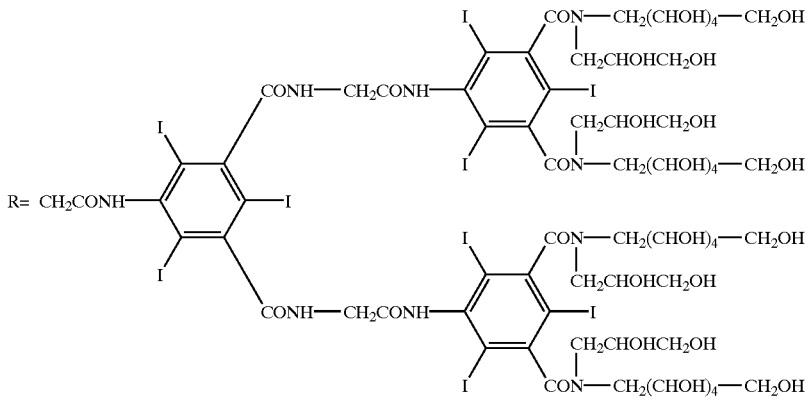

(a) 50 g of 1-deoxy-1-(2,3-dihydroxypropyl)amino-D-galactitol are dissolved in 300 ml of dimethylacetamide at 120° C. and then 38 g of 5-(phthalimidoacetamido)-2,4,6-triiodoisophthalic acid chloride (prepared according to U.S. Pat. No. 4,283,381) and 17 ml of triethylamine are rapidly added at 80° C. After stirring for 5 hours at 80° C., the mixture is filtered at room temperature, the filtrate is introduced into 800 ml of isopropyl alcohol and the precipitate is isolated and dried.

The excess starting aminoalcohol is removed by chromatographing the aqueous solution of this prepitate through $H^+$ resin.

The phthalimide group is hydrazinolysed in aqueous medium to produce N,N'-bis(2,3,4,5,6-pentahydroxyhexyl)-N,N'-bis(2,3-dihydroxypropyl)-2,4,6-triiodo-5-(glycylamino)isophthalimide.

(b) 23 g of 5-(phthalimidoacetamido)-2,4,6-triiodoisophthalic acid chloride and 12 ml of triethylamine are added to 70 g of the amine obtained in (a) in solution in 200 ml of dimethylacetamide. After stirring for 24 hours at room temperature, the reaction mixture is poured into 1500 ml of isopropyl alcohol and the precipitate formed is isolated.

The crude phthalimide thus obtained, in solution in 160 ml of water at pH 5, is chromatographed through 650 g of Amberlite® XAD 16 resin, elution being carried out with a water/methanol (65/35 v/v) mixture. The amino group of the phthalimide is deprotected by hydrazinolysis: 57 g of phthalimide are treated with 3 ml of $NH_2$—$NH_2$ in 200 ml of water at 80° C.; after 3 hours, the phthalohydrazide is precipitated at pH 1 and the filtrate is evaporated to give an oil, which is purified by precipitation from ethanol and chromatographed through anionic-exchange resin (weakly basic Amberlite®) and cationic-exchange resin (IMAC HPIII from Röhm & Haas).

Analytical HPLC: Column No. 2; Eluent No. 8: $H_2O$/$CH_3CN$; 95% to 80% gradient over 45 minutes.

$t_r$: 33 to 49 minutes.

Under the same conditions, the amine obtained in (a) is defined by $t_r$=6 to 16 minutes.

Another mixture of isomers of the compound F can be prepared by applying the above procedure to 1-deoxy-1-(2,3-dihydroxypropyl)amino-D-glucitol.

In that which follows, the preparation of certain chelates of the invention is described by way of illustration.

EXAMPLE 1

3,6,9,15-Tetraazabicyclo-[9.3.1]pentadeca-1(15),11,13-triene-3,6,9-tri(α-glutaric acid) (formula V) and gadolinium complex:

1. 20 g of the heterocycle 3,6,9,15-tetraazabicyclo[9.3.1]pentadeca-1(15),11,13-triene are dissolved in 570 ml of acetonitrile and, at 80° C., 34 g of $Na_2CO_3$ and then, slowly, 77 g of methyl α-bromoglutarate in solution in 110 ml of acetonitrile are introduced. After 24 hours at its reflux temperature, the mixture is filtered at approximately 20° C. and the filtrate is brought to dryness. The residual solid is purified by silica chromatography, elution being carried out with an ethyl acetate/heptane (6/4, v/v) mixture. w=25 g.

2. Hydrolysis:

A solution of 5.8 g of the product obtained in the preceding stage in 15 ml of methanol, to which 42 ml of a 5N aqueous NaOH solution have been added, is maintained at 70° C. for 3 days. On adding 100 ml of water, the pH of the solution is brought to 6.5 by addition of a cationic resin ($H^+$) and then, after filtration, the solution is brought into contact with an anionic resin ($OH^-$). The product is released from the resin with an acetic acid/water (50/50, v/v) mixture.

HPLC: Column No. 2; Eluent No. 6: $H_2SO_4$ in $H_2O$ (0.037N)/$CH_3CN$; Gradient from 100% to 20% (v/v) over 50 minutes; flow rate 1 ml/minute;

$t_r$=12.5 to 13.5 minutes (several peaks).

3. Complexing:

3 g of the acid and 1.9 g of $GdCl_3$ are dissolved in 54 ml of water. The mixture is brought to 55° C. and the pH is brought to 5 by addition of an N aqueous NaOH solution. After 3 hours at 60° C., the mixture is filtered at approximately 20° C. and then poured into 100 ml of ethanol. The sodium salt of the complex is isolated to give a yield of 70%.

HPLC: Column No. 2; Eluent No. 6;

$t_r$=15 to 16 minutes (several peaks).

EXAMPLE 2

Compound of formula I with

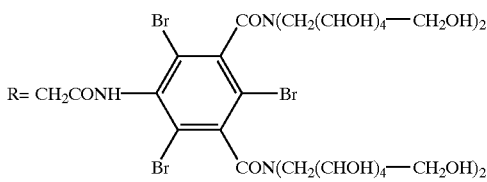

0.5 g of the complex obtained in Example 1 and 3.15 g of the amine $RNH_2$ are introduced into 10 ml of water. The pH is brought to 6 by addition of an aqueous NaOH solution (0.1N) before adding 2 equivalents of 1-(3-dimethylaminopropyl)-3-ethylcarbodiimide hydrochloride (EDCI). After 3 hours at 40° C., the mixture is poured into 100 ml of ethanol and the precipitate is isolated.

Purification is carried out by ultrafiltration of its aqueous solution through a polyethersulphone membrane, with a cutoff threshold of 3 Kdaltons, followed by chromatographing on a column of silanized silica, LiChroprep® (RP2 and RP18 (50/50) reference mixture) from Merck, elution being carried out with a water/$CH_3CN$ mixture (gradient from 98% to 95%).

w=0.8 g.

HPLC: Column No. 2; Eluent No. 7: $H_2O/CH_3CN$;

Gradient from 98% to 70% (v/v) over 20 minutes; flow rate 1 ml/minute;

$t_r$=10 minutes.

EXAMPLE 3

Compound of formula I with

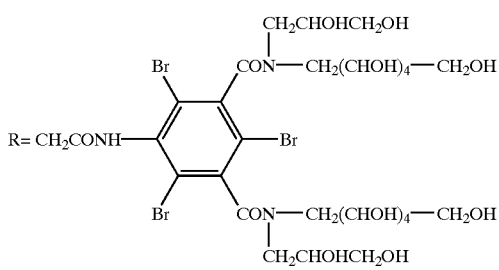

A) Galactose derivative:

8.3 g of the compound A and 1.8 g of the complex obtained in Example 1 are dissolved in 100 ml of water. After having brought the pH to 6 by addition of an N aqueous HCl solution, 2.7 g of EDCI and 150 mg of sodium salt of N-hydroxysuccimide-3-sulphonic acid (NHS) are added. After stirring for 2 hours, the solution is poured into 300 ml of ethanol and the precipitate formed is isolated. It can be purified by preparative high pressure liquid chromatography on LiChrospher® C18, 100 Å, 12 μm (Merck) or by ultrafiltration.

Analytical HPLC: Column No. 2; Eluent No. 7;

$t_r$=12 minutes.

A') Glucose derivative:

By reaction of the compound A' with the complex obtained in Example 1 under the same operating conditions as for A, the corresponding crude compound of formula I is obtained. The latter can be purified by chromatography on a Purospher® RP18 column, elution being carried out with an $H_2O/CH_3CN$ mixture.

Final yield: 40%.

EXAMPLE 4

Compound of formula I with

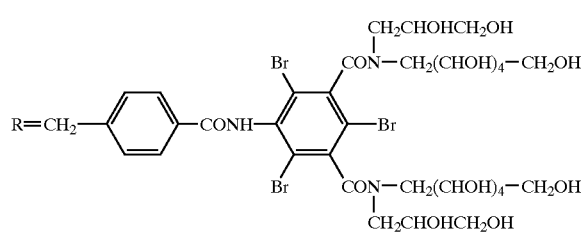

2.5 g of the complex obtained according to Example 1 and 11 g of the compound B are dissolved in 60 ml of water; after addition of a 1N aqueous HCl solution until a pH of 6 is obtained, 45 ml of acetone, 0.5 g of hydroxybenzotriazole hydrate (HOBT) and 2.3 g of EDCI are added. The reaction mixture is stirred for 4 hours at approximately 20° C. while periodically bringing the pH back to 6 by addition of N aqueous NaOH solution. The solution is poured into 500 ml of ethanol and the isolated precipitate is dried. w=11.7 g.

The product is purified by preparative chromatography under pressure on a LiChrospher® C18 column, 10 μm; l=25 cm; d=50 mm (Merck), elution being carried out with a water/acetonitrile mixture with a gradient from 95% to 90% over 20 minutes and then to 85% over 25 minutes; flow rate 80 ml/minute.

Yield =45%.

Analytical HPLC: Column No. 2; Eluent No. 8: $H_2O/CH_3CN$; 95% to 80% gradient over 45 minutes;

$t_r$=31 minutes.

EXAMPLE 5

Compound of formula I with

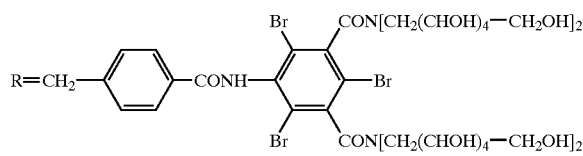

prepared according to the method described in Example 4 but with the compound C.

Analytical HPLC: Column No. 2; Eluent No. 8.

Retention time 25 to 29 minutes.

EXAMPLE 6

Compound of formula I with

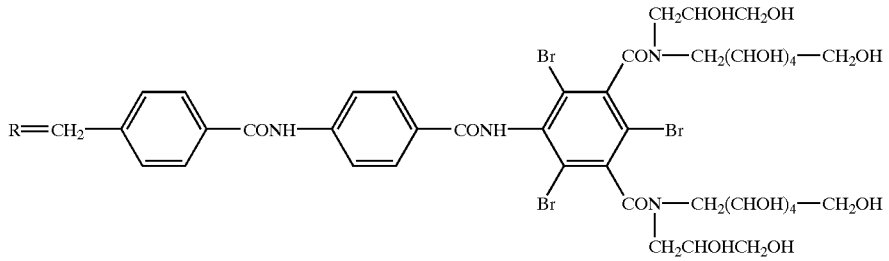

1.6 g of the complex of Example 1 and 7 g of the amine E are dissolved in 40 ml of water. 0.3 g of HOBT and 1.5 g of EDCI are introduced at pH 6, followed by 30 ml of acetone. The mixture is stirred for 4 hours while maintaining the pH at approximately 6. The precipitate obtained by pouring the solution into 450 ml of ethanol is purified by high pressure preparative chromatography on a Purospher® column; l=250 mm; d=40 mm; RP18; 10 μm; 120 Å (Merck), elution being carried out with a water/acetonitrile mixture (90% to 80% gradient over 5 minutes); flow rate=80 ml/minutes.

Analytical HPLC: Column No. 3: Purosphero; RP18 end-capped; 5 μm; l=250 mm; d=4 mm (Merck); eluent No. 7 but gradient from 85% to 70% over 10 minutes (v/v) after 20 minutes;

$t_r$=29 minutes.

EXAMPLE 7

Compound of formula I with

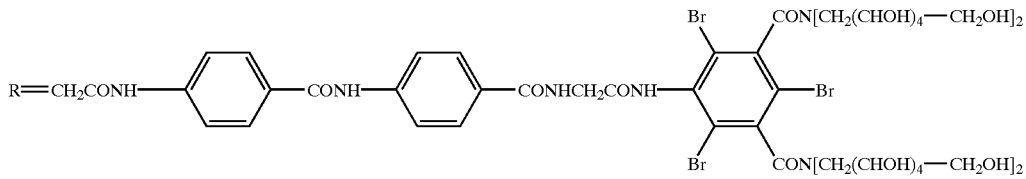

The product is prepared by applying the method described in the preceding examples with the amine D.

Analytical HPLC: Column No. 4: Zorbax® 300SB-C18; l=250 mm, d=4 mm, Hewlett Packard®;

Eluent No. 1 but 90% to 82% gradient over 60 minutes;

$t_r$=42 to 49 minutes.

EXAMPLE 8

Compound of formula I with

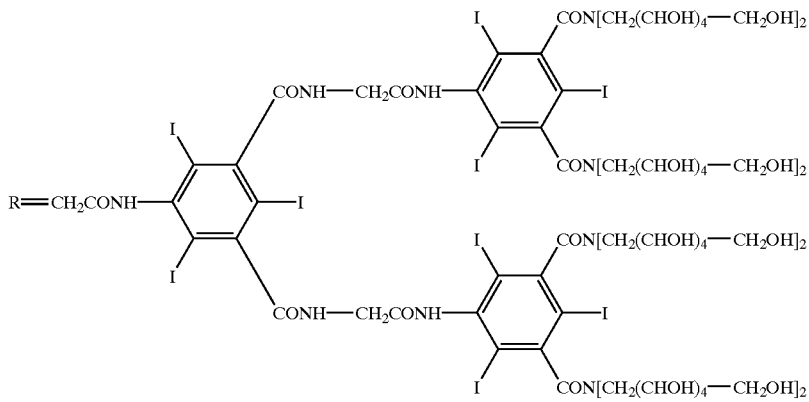

The product is prepared by using amidation conditions analogous to those of the preceding examples.
Analytical HPLC: Column No. 2
Eluent No. 7 but 98% to 85% gradient over 40 minutes;
$t_r$=24 minutes.

EXAMPLE 9

Compound of formula I with

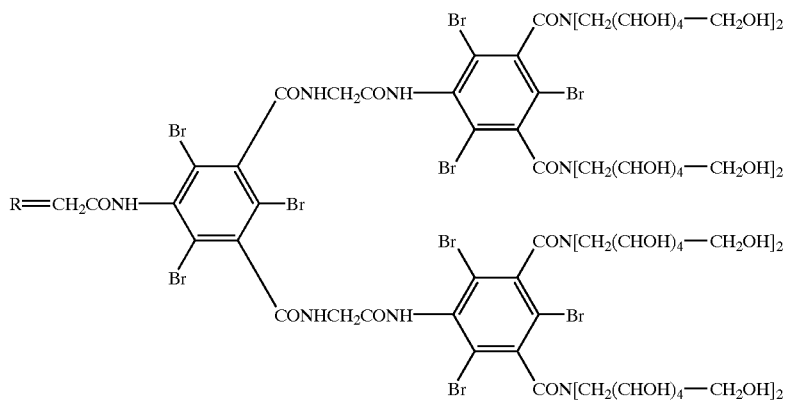

Analytical HPLC: Column No. 2; Eluent: $H_2O/CH_3CN$ in 95/5 (v/v) and then gradient after 20 minutes to reach 85/15 over 10 minutes; flow rate=1 ml/minute.
$t_r$=26 minutes.

EXAMPLE 10

Compound of formula I with

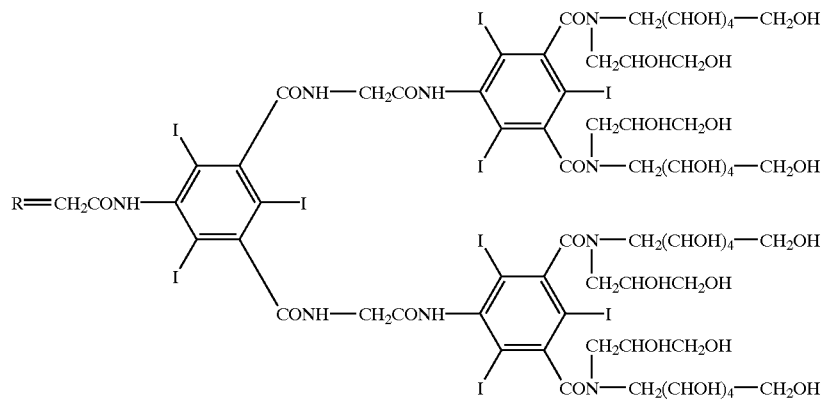

prepared by reacting the compound F with the complex of Example 1:

1 g of complex and 12 g of amine F are dissolved in 200 ml of water and the pH is brought to 6 by addition of a 6N aqueous HCl solution. 0.1 g of EDCI and 0.25 g of HOBT are then introduced; the mixture is kept stirred for 48 hours, the pH being brought back to 6 by addition of a 2% aqueous $NaHCO_3$ solution. The final crude product is isolated by introducing the mixture into 10 volumes of ethanol and is purified by preparative chromatography on a Purospher® RP18, 10 μm, 120 Å column (Merck), elution being carried out with an $H_2O/CH_3CN$ mixture. Yield: 30%.

Analytical HPLC: Column No. 2; Eluent No. 8
$t_r$=12 minutes.

What is claimed is:

1. A metal chelate of a compound of formula

I

RHNOC—$(CH_2)_2$—HC—N... (structure with pyridine, HOOC, COOH, CH—$(CH_2)_2$—CONHR, CH—$(CH_2)_2$—CONHR, COOH)

wherein

R has the formula

II

—Z—[phenyl—Z']$_p$—[phenyl—Z'']$_q$—(phenyl with $R_1, R_2, R_3, R_4, R_5$)

and

Z is a bond or a group selected from the group consisting of $CH_2$, $CH_2$—CO—NH and $(CH_2)_2$—NH—CO, Z' is a bond or a radical selected from the group consisting of O, S, NQ, $CH_2$, CO, CO—NQ, NQ—CO, NQ—CO—NQ and CO—NQ—$CH_2$—CO—NQ, Z'' is a bond or a radical selected from the group consisting of CO—NQ, NQ—CO and CO—NQ—$CH_2$—CO—NQ groups, p and q are integers, the sum of which has a value from 0 to 3, $R_1, R_2, R_3, R_4, R_5$, independently of one another, are selected from the group consisting of H, Br, Cl, I, CO—$NQ_1Q_2$ and $NQ_1$—CO—$Q_2$, $Q_1$ and $Q_2$, which are identical or different, being H or ($C_1$–$C_6$) alkyl optionally interrupted by one or more oxygen atoms and at least one of the $R_1$ to $R_5$ groups being an amido group, or $R_1, R_3,$ and $R_5$ are, independently of one another, H, Br, Cl or I, and $R_2$ and $R_4$, which are identical, have the formula

III (structure: phenyl with $R_1'$, CO—$NQ_1'Q_2'$, —Z'''—, $R_3'$, $R_4'$, CO—$NQ_1'Q_2'$)

such that Z''' is a radical selected from the group consisting of CO—NQ, CO—NQ—$CH_2$—CO—NQ, CO—NQ—$CH_2$, CO—NQ$(CH_2)_2$—NQ—CO and NQ—CO—NQ, and $R'_1, R'_3$ and $R'_5$, which are identical or different, are H, Br, Cl or I, and $Q'_1$ and $Q'_2$, which are identical or different, are H or ($C_1$–$C_6$) alkyl optionally interrupted/by one or more oxygen atoms, Q is H or ($C_1$–$C_4$) alkyl, the alkyl groups being optionally mono- or polyhydroxylated, and wherein the metal of the metal chelate is a paramagnetic ion, a radioactive ion, or a transmetallation-effecting ion.

2. The chelate of claim 1 of a compound of formula I, wherein p and q are 0 and $R_2$ and $R_4$ are CO—$NQ_1Q_2$.

3. The chelate of claim 1 of a compound of formula I, wherein p and q are 0 and $R_2$ and $R_4$ are CO—$NQ_1Q_2$ and each CO—$NQ_1Q_2$ group has from 6 to 10 OH groups.

4. The chelate of claim 1 of a compound of formula I, wherein p and q are 0, $R_1, R_3$ and $R_5$ are identical and are selected from Br and I, and $R_2$ and $R_4$ are CO—$NQ_1Q_2$ and each CO—$NQ_1Q_2$ group has from 6 to 10 OH groups.

5. The chelate of claim 1 of a compound of formula I, wherein the sum p+q is not 0 and $R_2$ and $R_4$ have not the formula III.

6. The chelate of claim 1 of a compound of formula I, wherein the sum p+q is not 0 and any CO—$NQ_1Q_2$ group when present has from 6 to 10 OH groups and $R_2$ and $R_4$ have not the formula III.

7. The chelate of claim 1 of a compound of formula I, wherein the sum p+q is not 0, $R_1, R_3$ and $R_5$ are identical and are selected from the group consisting of Br and I, and $R_2$ and $R_4$ are CO—$NQ_1Q_2$, $R_2$ and $R_4$ each having from 6 to 10 OH groups.

8. The chelate of claim 1 of a compound of formula I, wherein Z is $CH_2$ or $CH_2$—CO—NH, Z' is a radical selected from the group consisting of CO—NH, CO—NH—$CH_2$—CO—NH and NH—CO—NH, Z'' is selected from the group consisting of CO—NH and CO—NH—$CH_2$—CO—NH and Z''' when it is present, is CO—NH or CO—NH—$CH_2$CO—NH.

9. The chelate of claim 1 of a compound of formula I, wherein Z is $CH_2$ or $CH_2$—CO—NH; Z' is a radical selected from the group consisting of CO—NH, CO—NH—$CH_2$—CO—NH and NH—CO—NH; Z'' is a radical selected from the group consisting of CO—NH and CO—NH—$CH_2$—CO—NH; $R_2$ and $R_4$ are CO—$NQ_1Q_2$, $R_2$ and $R_4$ each having from 6 to 10 OH groups; and $R_1, R_3$ and $R_5$ are identical and are selected from the group consisting of Br and I.

10. The chelate of claim 1 of a compound of formula I, wherein the sum p+q is 1 or 2 and $R_2$ and $R_4$ have not the formula III.

11. The chelate of claim 6, wherein the sum p+q is 1 or 2.

12. The chelate of claim 7, wherein the sum p+q is 1 or 2.

13. The chelate of claim 8, wherein the sum p+q is 1 or 2.

14. The chelate of claim 9, wherein the sum p+q is 1 or 2.

15. The chelate of claim 1 the compound of formula I, wherein $R_2$ and $R_4$ are CO—$NQ_1Q_2$ and $Q_1$ and $Q_2$ are polyhydroxylated ($C_2$–$C_6$) alkyl groups optionally interrupted by an oxygen atom.

16. The chelate of claim 1 of a compound of formula I, wherein Z is $CH_2$ or $CH_2$—CO—NH, Z' and Z" are selected from the group consisting of CO—NH and CO—NH—$CH_2$—CO—NH, p and q are equal to 1 and $R_2$ and $R_4$ are CON $Q_1Q_2$.

17. The chelate of claim 16, wherein $R_2$ and $R_4$ together have from 6 to 20 OH groups.

18. The chelate of claim 16, wherein $R_1$, $R_3$, and $R_5$ are identical and are selected from the group consisting of Br and I, and $R_2$ and $R_4$ each have from 6 to 10 OH groups.

19. The chelate of claim 1 of a compound of formula I, wherein p and q are 0, $R_2$ and $R_4$ have the formula III and $R_1$, $R_3$, and $R_5$ are identical and are selected from the group consisting of Br and I.

20. The chelate of claim 1 of a compound of formula I, wherein p=q=0; Z=$CH_2$CONH; and

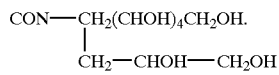

$$CON-\underset{\underset{CH_2-CHOH-CH_2OH}{|}}{CH_2(CHOH)_4CH_2OH.}$$

21. The chelate of claim 1 of a compound of formula I, wherein p=1 or 2; q=0; Z—$CH_2$; Z'=CONH; $R_1$=$R_3$=$R_5$=Br;

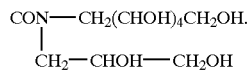

$$CON-\underset{\underset{CH_2-CHOH-CH_2OH}{|}}{CH_2(CHOH)_4CH_2OH.}$$

22. The chelate of claim 1 of a compound of formula I, wherein p=q=1; Z=$CH_2$CONH; Z'=CONH; Z"=CONH—$CH_2$CONH; $R_1$=$R_3$=$R_5$=Br; $R_2$=$R_4$=CON($CH_2$(CHOH)$_4$ $CH_2$OH)$_2$.

23. The chelate of claim 1 of compound of formula I, wherein p=q=0; Z=$CH_2$CONH; $R_1$=$R_3$=$R_5$=Br;

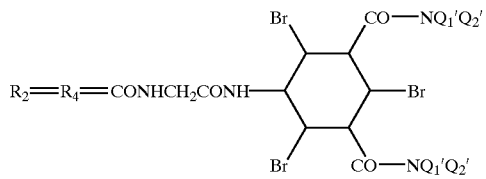

$Q'_1$=$Q'_2$=$CH_2$(CHOH)$_4$$CH_2$OH
or $Q'_1$=$CH_2$(CHOH)$_4$$CH_2$OH and $Q'_2$=$CH_2$—CHOH—$CH_2$OH.

24. The chelate of claim 1 of a compound of formula I wherein the metal is $Gd^{3-}$ or $Mn^{2+}$.

25. The chelate of claim 1 of a compound of formula I wherein the metal is $Gd^{3+}$.

26. The chelate of claim 19 of a compound of formula I wherein the metal is $Gd^{3+}$.

27. The chelate of claim 20 of a compound of formula I wherein the metal is $Gd^{3+}$.

28. The chelate of claim 21 of a compound of formula I wherein the metal is $Gd^{3+}$.

29. The chelate of claim 22 of a compound of formula I wherein the metal is $Gd^{3+}$.

30. The chelate of claim 23 of a compound of formula I wherein the metal is $Gd^{3-}$.

31. A metal chelate of the compound of formula

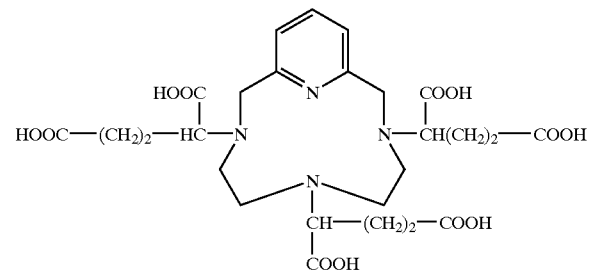

wherein the metal of the metal chelate is a paramagnetic ion, a radioactive ion, or a transmetallation-effecting ion, and its salts with an inorganic or organic base.

32. The chelate as claimed in claim 31, wherein the metal is $Gd^{3+}$.

33. A process for the preparation of the compounds of formula I of claim 1, which comprises reacting the macrocycle of formula

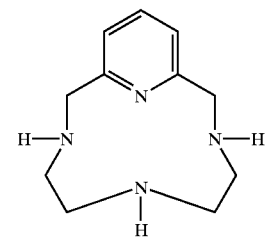

with a compound of formula R'OOC—CHX—(CH$_2$)$_2$ —COOR', wherein X is a leaving group and R' is H or ($C_1$–$C_3$) alkyl, and hydrolysing the ester functional groups when R' is other than H, then reacting with a metal salt or oxide, wherein the metal of the metal salt or oxide is a paramagnetic metal, a radioactive metal, or a transmetallation-effecting metal, in order to obtain the chelate of the product formed or one of its salts with a base, and reacting the chelate with the amine $RNH_2$ in the presence of an agent for activating the carboxylic acid groups.

34. A composition for diagnostic imaging comprising a chelate as claimed in claim 1 with a pharmaceutically acceptable vehicle and optionally the usual formulation additives.

35. A composition for nuclear magnetic resonance imaging comprising a gadolinium chelate as claimed in claim 1.

* * * * *